(12) United States Patent
Espinoza et al.

(10) Patent No.: US 6,951,893 B2
(45) Date of Patent: Oct. 4, 2005

(54) HEAT TREATED FISCHER-TROPSCH CATALYST PARTICLES

(75) Inventors: Rafael Luis Espinoza, Sasolburg (ZA); Philip Gibson, Sasolburg (ZA); Jan Hendrik Scholtz, Vanderbijlpark (ZA)

(73) Assignee: Sasol Technology (Pty) Ltd, Johannesburg (ZA)

( * ) Notice: Subject to any disclaimer, the term of this patent is extended or adjusted under 35 U.S.C. 154(b) by 0 days.

(21) Appl. No.: 10/677,588

(22) Filed: Oct. 2, 2003

(65) Prior Publication Data

US 2004/0072917 A1 Apr. 15, 2004

Related U.S. Application Data

(63) Continuation of application No. 09/601,076, filed on Feb. 20, 2001, now Pat. No. 6,716,790.
(60) Provisional application No. PCT/GB98/03004, filed on Oct. 7, 1998.

(30) Foreign Application Priority Data

Apr. 1, 1998 (ZA) .............................................. 98/2737

(51) Int. Cl.$^7$ .............................................. C07C 27/00
(52) U.S. Cl. ....................................... 518/719; 518/720
(58) Field of Search ................................. 518/719, 720

(56) References Cited

U.S. PATENT DOCUMENTS

| | | | |
|---|---|---|---|
| 4,621,102 A | 11/1986 | Fiato et al. | |
| 5,118,715 A | 6/1992 | Iglesia et al. | |
| 5,324,335 A | 6/1994 | Benham et al. | |
| 5,504,118 A | 4/1996 | Benham et al. | |
| 5,545,674 A | 8/1996 | Behrman et al. | |
| 5,645,613 A | 7/1997 | Benham et al. | |
| 5,763,716 A | * 6/1998 | Benham et al. ............. | 585/315 |

OTHER PUBLICATIONS

H. Kolbel, et al., "Feedstock for Chemical Industry by Selective Fischer–Tropsch–Synthese", 1978, Society of Automotive Engineers, p. 482–486.

Maiti, et al., *Iron/Manganese Oxide Catalysts for Fischer–Tropsch Synthesis Part II: Crystal Phase Composition, Activity and Selectivity*, Applied Catalysis, 16 (1985) 215–225.

\* cited by examiner

*Primary Examiner*—J. Parsa
(74) *Attorney, Agent, or Firm*—Knobbe Martens Olson & Bear LLP

(57) ABSTRACT

The invention provides heat treated self-supported precipitated iron-based Fischer-Tropsch catalyst particles. The particles of the present invention are breakage resistant and exhibit superior synthesis performance. The invention also provides a method for producing said particles and a process for using said particles.

15 Claims, 6 Drawing Sheets

Table 1: Catalyst physical properties as a function of calcination temperature

| Sample | Calc.temp °C | Area m²/g | Pore vol cc/g | % fines<22μm after JI |
|---|---|---|---|---|
| Pilot Plant catalyst | uncalc | 288 | 0.03 | 11.6 |
| | 300 | 286 | 0.64 | 2.8 |
| | 400 | 262 | 0.63 | 3.7 |
| | 500 | 243 | 0.60 | 2.1 |
| | | | | |
| Commercial catalyst | uncalc | 293 | 0.62 | 11.4 |
| | 300 | 267 | 0.61 | 1.1 |
| | 400 | 247 | 0.67 | 1.6 |
| | 500 | 225 | 0.60 | 1.9 |
| Pilot Plant Rotary Kiln | | | | |
| Commercial catalyst | uncalc | 289 | 0.60 | 12.2 |
| | 385 | 241 | 0.54 | 5.8 |

Table 2: Behaviour after repeated jet impingement

| | Increase in % fines< 22μm | |
|---|---|---|
| | Uncalcined | Calcined at 300°C |
| Before Jet Impingement | 0 | 0 |
| After Jet Impingement 1 | 11.6 | 2.8 |
| After Jet Impingement 2 | 29.4 | 18.5 |
| After Jet Impingement 3 | 22.4 | 19.5 |

Table 3: Mössbauer spectroscopic parameters

| | Uncalcined sample | Calcined sample |
|---|---|---|
| Hyperfine field (H) (T) | 517.6 | 515.3 |
| | 496.9 | 495.3 |
| | 473.8 | 472.6 |
| | 444.4 | 442.5 |
| Isomer shift ($\delta_1$) (mm.s$^{-1}$) | 0.757 | 0.761 |
| | 0.744 | 0.742 |
| | 0.717 | 0.711 |
| | 0.678 | 0.669 |
| Quadropole splitting ($\Delta E_Q$) (mm.s$^{-1}$) | 0.010 | 0.009 |
| | 0.018 | 0.013 |
| | 0.024 | 0.026 |
| | 0.021 | 0.024 |

Table 4: On line quantification of catalyst fines

| | Volume(%<) | |
|---|---|---|
| Particle diameter (μm) | Uncalcined catalyst | Calcined catalyst |
| 22 | 10.1 | 0.28 |
| 11 | 5.6 | 0.16 |
| 4 | 1.9 | 0.02 |

Table 5: Mechanical strength of dried samples

| Sample | % Moisture | % fines <22μm after J1 |
|---|---|---|
| Standard | 2.7 | 9.7 |
| Dried | 1.0 | 7.0 |
| Calcined | 1.3 | 1.5 |

Graph 1: Solid separation performance of uncalcined catalyst
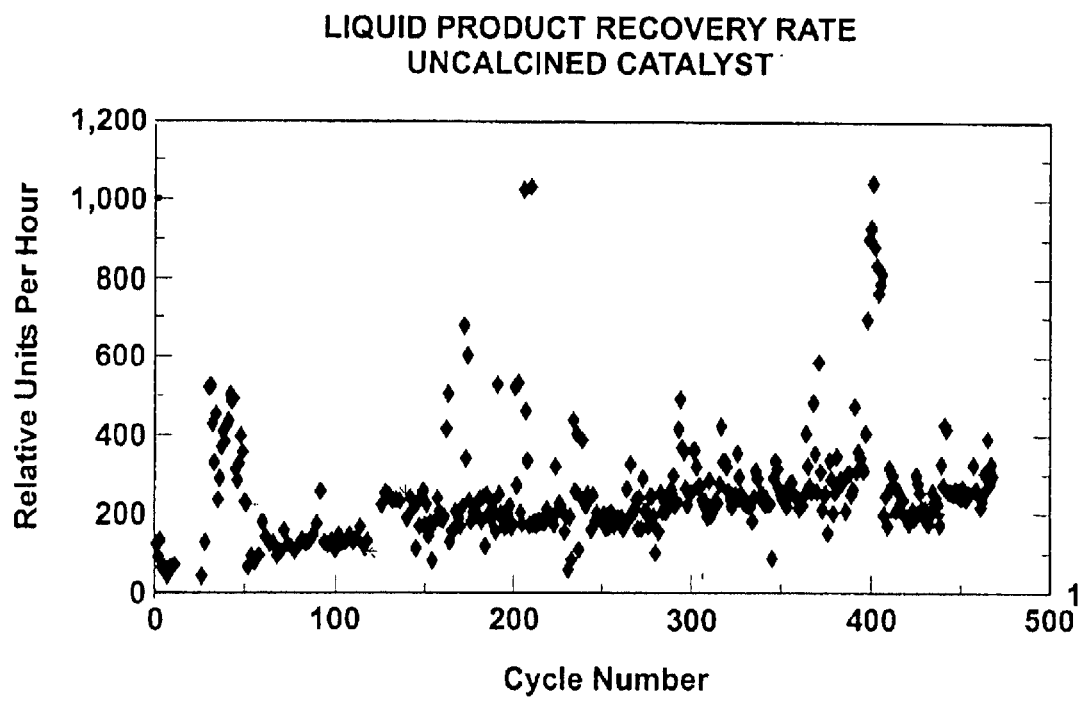
Graph 2: Solid separation performance of calcined catalyst
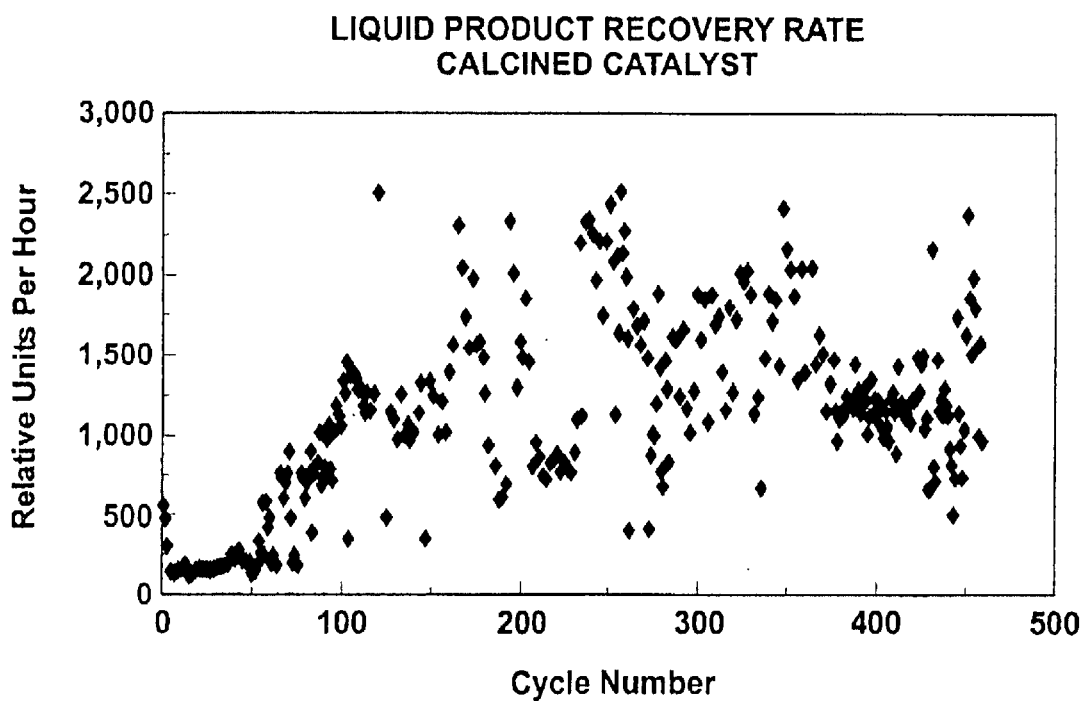

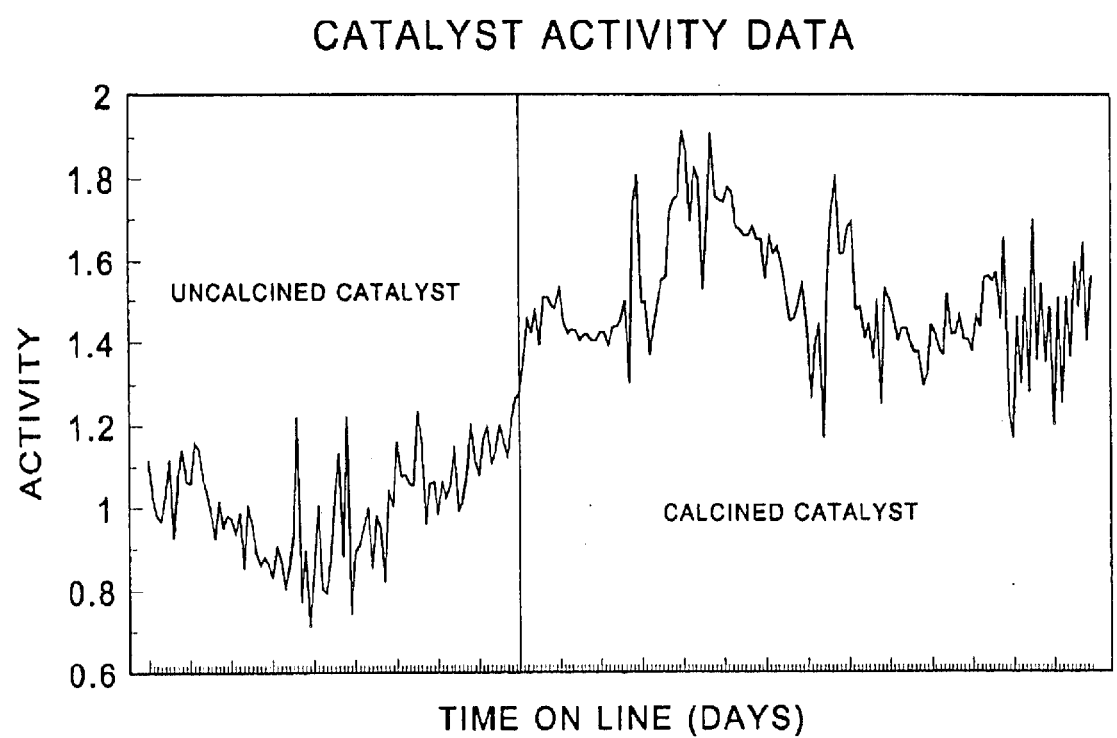
Graph 3: Increase in catalyst activity after addition of calcined catalyst

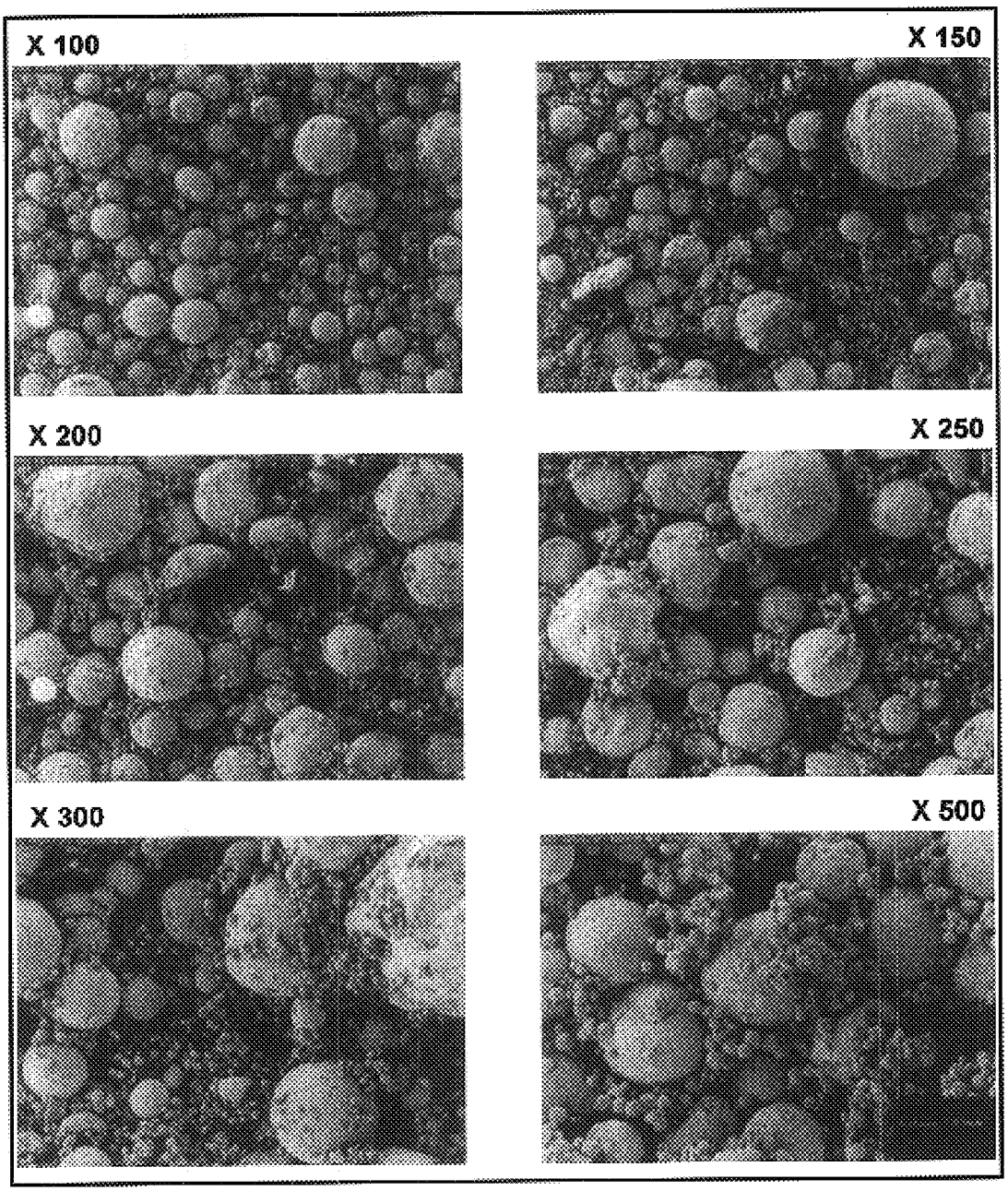
Micrograph 1: On line uncalcined catalyst particles

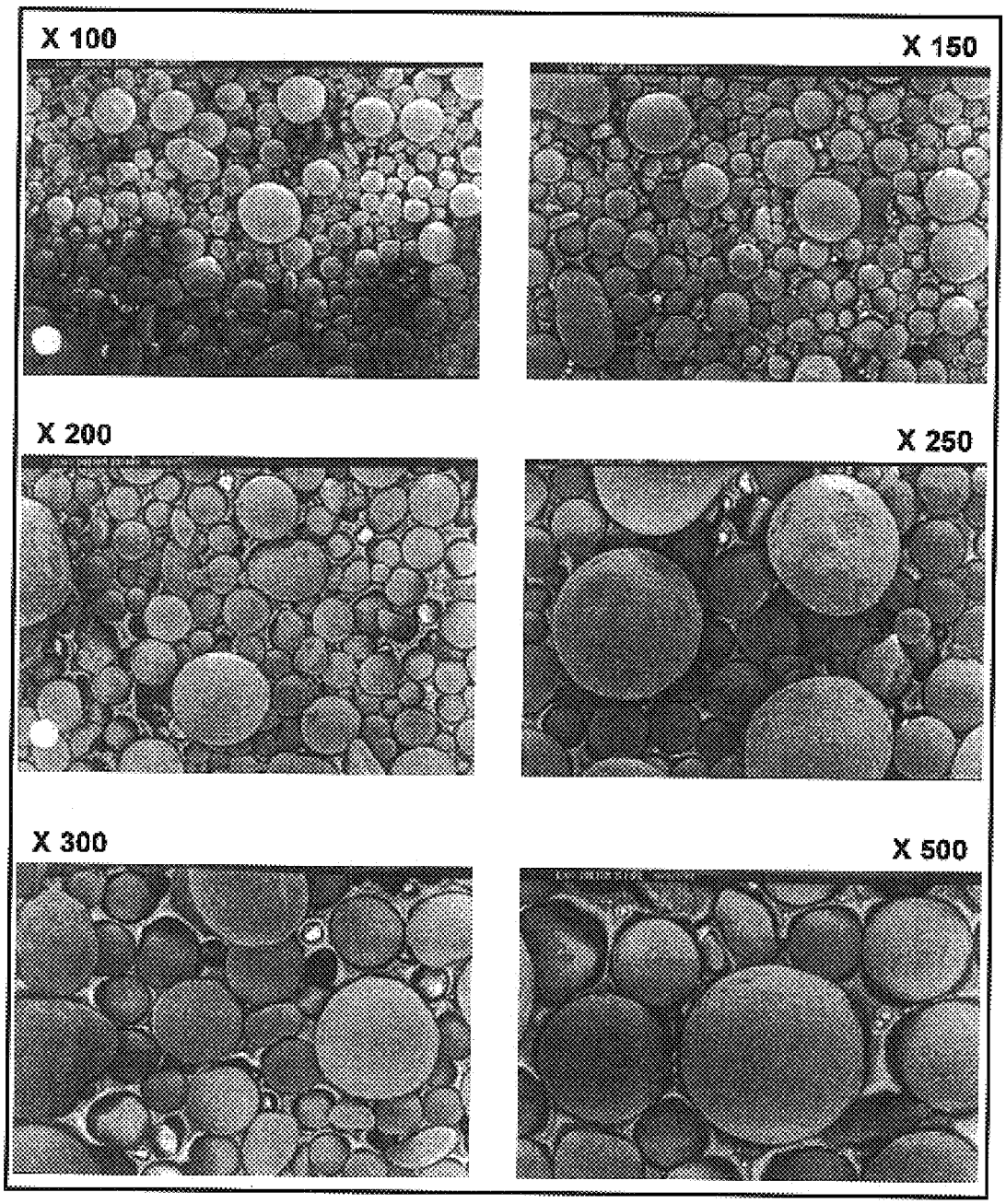
Micrograph 2: On line calcined catalyst particles

HEAT TREATED FISCHER-TROPSCH CATALYST PARTICLES

This application is a continuation of application No. 09/601,076, filed Feb. 20, 2001, U.S. Pat. No. 6,716,790 which is the national phase under 35 U.S.C. §371 of prior PCT International Application No. PCT/GB98/03004 which has an International filing date of Oct. 7, 1998, which designated the United States of America, and which was published by the International Bureau in English on Oct. 7, 1999, and which claims the benefit of South African Application No. 98/2737 filed Apr. 1, 1998.

This invention relates to catalysts. More particularly the invention relates to a method of making breakage resistant self-supported precipitated iron-based Fischer-Tropsch catalyst particles, to a method of making self-supported precipitated iron-based Fischer-Tropsch catalyst particles having superior synthesis performance or activity, to catalyst particles made according to the methods, and to the use of said catalyst particles in a slurry bed Fischer-Tropsch reactor.

BACKGROUND OF THE INVENTION

U.S. Pat. Nos. 5,324,335 and 5,504,118 disclose the production of roughly spherical iron-based Fischer-Tropsch catalyst particles having diameters in the range of between 1 and 50 microns which are annealed by heating in air at about 316° C. (600° F.) to drive off residual moisture and to stabilise the catalyst. The annealing step i.e. the heating and gradual controlled cooling, converts the Goethite to Hematite whereafter the catalyst may be activated and used. According to these patents, the annealing does not lead to a breakage resistant or a superior performance catalyst particle.

South African Patent No. 90/7530 discloses the production of an iron-based Fischer-Tropsch catalyst including from 1 to 80% by mass of activated carbon. This catalyst shows improved breakage resistance over conventional catalyst, particularly where the particle diameters are below about 45 micron. The catalyst particle of this patent does not have superior synthesis performance and is expected to hydrothermally sinter at about 300° C.

A need thus exists for breakage resistant iron-based Fischer-Tropsch catalyst particles, in particular for use in a low temperature Fischer-Tropsch process, such as that carried out in a slurry bed reactor, for the production of, amongst others, wax and other syncrudes, as well as chemicals. The breakage resistant self-supported precipitated iron-based Fischer-Tropsch catalyst particles will ideally inhibit the formation of catalyst fines in the reactor thereby maintaining the performance of the reactor and reduce the contamination of down stream processes and catalysts by the catalyst fines.

In this specification, unless the context clearly indicates to the contrary, the term "fines" when used in relation to catalysts and catalyst particles is to be understood to mean particles which due to their dimensions, when present at a concentration of about 30% of the total catalyst, tend to reduce the performance of the solid separation system of a Fischer-Tropsch slurry bed reactor. Typically fines have a diameter of less than about 45 microns, usually about 22 microns.

A further long felt need which exists is that for self-supported precipitated iron-based Fischer-Tropsch catalyst particles having superior synthesis performance or activity, in particular for use in a low temperature Fischer-Tropsch process, such as that carried out in a slurry bed reactor, for the production of wax and other syncrudes, as well as chemicals.

BRIEF SUMMARY OF THE INVENTION

It is well expected that heat treatment of self-supported precipitated catalyst particles has a negative effect on the activity thereof. In particular, the catalyst particle surface area and pore volume are likely to be reduced at temperatures above 250° C. Those skilled in the art therefore generally tend to avoid such heat treatment of such Fischer-tropsch catalyst material.

Surprisingly it has now been found that the breakage resistance and the synthesis performance or activity of self-supported precipitated iron-based Fischer-Tropsch catalyst particles can be increased by the heat treatment thereof at temperatures of at least 250° C.

Accordingly, the invention provides a method of producing self-supported precipitated iron-based catalyst particles for use in a Fischer-Tropsch slurry-bed process, the said particles being breakage resistant and thus inhibiting the formation of catalyst fines, the method including the heat treatment of the said particles at a temperature of at least 250° C.

The heat treatment may be calcination of the said particles at a temperature of at least 250° C.

The heat treatment of the said catalyst particles may be carried out at a temperature of between 250° C. and 500° C., preferably between 320° C. and 500° C., more preferably between 360° C. and 390° C., most preferably at 380° C.

According to a second aspect of the invention, there is provided a method of producing self-supported precipitated iron-based catalyst particles for use in a Fischer-Tropsch slurry-bed process, the catalyst particles having a superior synthesis performance or activity under low temperature Fischer-Tropsch slurry-bed operating conditions, the method including the heat treatment of the said catalyst particles at a temperature of at least 250° C.

The heat treatment temperature of the method may be between 250° C. and 500° C., preferably between 320° C. and 500° C., more preferably between 360° C. and 390° C., most preferably 380° C.

Typically the said catalyst particles are maintained at the heat treatment temperature for at least 0.1 hours, preferably between 0.2 and 12 hours, more preferably between 0.5 and 4 hours.

According to a further aspect of the invention there are provided self-supported precipitated iron-based catalyst particles for use in a Fischer-Tropsch slurry-bed process, the said catalyst particles being produced according to a method of heat treatment of the said catalyst particles as described above.

According to yet a further aspect of the invention, there is provided a method of maintaining the performance of a solid separation system of a Fischer-Tropsch process slurry bed reactor where a reduction in performance is caused by an increase in catalyst particle fines in the slurry bed reactor, the method including the use of the catalyst particles as described above.

According to yet a further aspect of the invention, there is provided a process for synthesis of syncrudes and/or chemicals, for example, waxes, the process comprising the step of contacting a suitable synthesis gas, at suitable temperatures and pressures in a Fischer-Tropsch slurry-bed reactor, with self-supported precipitated iron-based Fischer-Tropsch catalyst particles as described above.

The process may be carried out in a suitable vessel, with unreacted reactants and gaseous product being withdrawn above the slurry bed, and separated liquid product also being withdrawn from the vessel.

Typical suitable operating temperatures for the process are temperatures in the range 160° C. to 280° C., or even higher for production of lower boiling point product.

Typical suitable operating pressures are pressures in the range 18 Bar to 50 Bar.

DETAILED DESCRIPTION OF THE INVENTION

The invention will now be illustrated by means of the following non-limiting examples:

BRIEF DESCRIPTION OF THE DRAWINGS

Table 1 provides data regarding catalyst physical properties as a function of calcination temperature.

Table 2 provides data regarding catalyst behavior after repeated jet impingement conducted on a sample that was heat treated at 300° C.

Table 3 provides data regarding Mössbauer spectroscopic parameters for both untreated standard catalyst particles and heat treated catalyst particles.

Table 4 provides data regarding on line quantification of catalyst fines for untreated and heat treated catalyst particles.

Table 5 provides data regarding mechanical strength of dried samples.

Graph 1 provides liquid product recovery rate as a function of cycle number for a synthesis run with untreated catalyst particles.

Graph 2 provides liquid product recovery rate as a function of cycle number for a synthesis run with heat treated catalyst particles.

Graph 3 illustrates the increase in catalyst activity after addition of calcined catalyst.

Micrograph 1 provides micrographs of on line uncalcined catalyst particles at magnifications of ×100, ×150, ×200, ×250, ×300, and ×500.

Micrograph 2 provides micrographs of on line heat treated catalyst particles at magnifications of ×100, ×150, ×200, ×250, ×300, and ×500.

EXAMPLE 1

This example illustrates that the heat treatment of self-supported precipitated iron-based Low Temperature Fischer Tropsch catalyst particles for slurry bed application results in an increase in the mechanical strength of the said catalyst.

For a laboratory microscale operation, 250 grams of pilot plant and commercially prepared catalyst was placed in a porcelain dish in a muffle furnace. The furnace was subsequently heated to the desired heat treatment temperature at a heating rate of 1° C./min. The heat treatment or calcination temperature (as indicated in Table 1 below) was maintained for 4 hours after which the furnace was allowed to cool down to below 100° C.

For larger scale operation the catalyst was fed from a hopper at room temperature to a portable pilot plant scale rotary kiln. This kiln had a refractory lining and was electrically heated. The dimensions of this equipment were as follows: length=2.1 m, diameter=0.47 m, inclination=2°, rotational speed=1 rpm. The average temperature inside the kiln was controlled at 385° C. The feed rate was varied around 30 kg/h which resulted in a residence time of close to 1 hour. 1500 kg of catalyst was heat treated in this manner.

A sample of catalyst particles that were heat treated according to the manner described above was subjected to a Jet Impingement test. In this test a jet of air is used to impinge fresh catalyst particles against a plate. The smaller than 22 micron fraction of jet impinged sample is normally taken as a measure of the catalyst particle mechanical strength. Table 1 shows the results that were achieved from this test. Standard pilot plant prepared catalyst particles, and standard commercially prepared catalyst particles were used as reference materials.

Table 2 also reflects the results obtained from a repeated jet impingement test conducted on a sample that was heat treated at 300° C. Repeated jet impingement results indicated that the heat treated catalyst particles are stronger even after the initial break-up. It can be concluded that heat treatment induces strength to the whole particle, and not only to the outer shell of the particle.

EXAMPLE 2

This example illustrates that heat treatment of standard self-supported precipitated iron based Low Temperature Fischer Tropsch slurry bed catalyst particles does not alter the iron phase composition nor the crystallinity of the said catalyst particles; but rather promotes the enhancement of the catalyst particles' mechanical strength.

The phase composition and relative crystallite size of both the untreated standard catalyst particles and the heat treated samples were determined by Mössbauer spectroscopy at 4.2 K. The parameters are presented in Table 3.

Both samples can be described as highly dispersed Fe(III) oxide. The Fe-phase has been identified as $\alpha$-$Fe_2O_3$. The particles display superparamagnetic behaviour and from the quadropole splitting parameter the size of the primary particles was estimated as between 2 and 4 nm.

At 77 K the heat treated sample shows a slight increase in the $\Delta$ value, indicating a corresponding decrease in the primary particle size. Based on these results it would seem as if the heat treatment causes a restructuring or reordering of the ions making up the primary particle, thus leading to a state of lower energy i.e. a stronger particle.

EXAMPLE 3

This example illustrates that heat treatment of the catalyst particles results in a major improvement of the solid separation system performance of said catalyst particles as experienced in a semi-works pilot plant reactor.

The liquid product recovery rate as a function of cycle number for a synthesis run with untreated catalyst particles is depicted in Graph 1. The separation rate levels obtained from a synthesis run operating with these standard catalyst particles only reached a maximum of 350 relative units per hour.

Data for a similar synthesis run with heat treated catalyst is presented in Graph 2. The average liquid product recovery rate is clearly above 1000 relative units per hour.

EXAMPLE 4

This specific example illustrates that calcining or heat treating standard self-supported precipitated iron-based Low Temperature Fischer-Tropsch catalyst particles for slurry bed application results in a significant reduction of the amount of fines that the catalyst particles generate under normal Fischer-Tropsch synthesis conditions.

Particle size distributions of representative on line catalyst particle samples were obtained for periods when untreated and heat treated catalyst particles were run respectively as outlined in example 3 above. A comparison of the catalyst fines content is presented in Table 4. The heat treated catalyst clearly shows a dramatic decrease in the amount of fines present in the reactor.

Scanning electron micrographs of the above mentioned untreated and heat treated on-line catalyst particle samples are presented in Micrographs 1 and 2 respectively. The absence of fine catalyst particles in the heat treated sample is once again obvious for the heat treated version.

EXAMPLE 5

This example shows that there is a marked increase in activity of standard self-supported precipitated iron-based Fischer-Tropsch catalyst particles upon heat treatment. This is elegantly illustrated in Graph 3. The catalyst activity shows a continuous increase after the change to heat treated catalyst particles which is indicated by a vertical bar in Graph 3.

EXAMPLE 6

This example illustrates that removal of residual moisture from freshly prepared catalyst particles does not lead to mechanically stronger catalyst particles.

A sample of untreated standard catalyst particles was treated in a vacuum oven at 100° C. until the moisture content was half the original value. Both the untreated and the vacuum dried samples were subsequently subjected to a Jet Impingement (JI) test in order to measure their mechanical strength. The results are compared with a heat treated example in Table 5.

What is claimed is:

1. A process for synthesis of a Fischer-Tropsch product, the process comprising:

providing self-supported precipitated $\alpha$-$Fe_2O_3$-based Fischer-Tropsch catalyst particles, wherein the self-supported precipitated $\alpha$-$Fe_2O_3$-based Fischer-Tropsch catalyst particles are produced by heat treating precipitated $\alpha$-$Fe_2O_3$-based particles at a temperature of from 320° C. to 500° C.; and contacting a synthesis gas with the self-supported precipitated $\alpha$-$Fe_2O_3$-based Fischer-Tropsch catalyst particles in a Fischer-Tropsch slurry-bed reactor, whereby a Fischer-Tropsch product is obtained.

2. The process of claim 1, wherein heat treating precipitated $\alpha$-$Fe_2O_3$-based particles is carried out at a temperature of from 360° C. to 500° C.

3. The process of claim 1, wherein heat treating precipitated $\alpha$-$Fe_2O_3$-based particles is carried out at a temperature of from 360° C. to 390° C.

4. The process of claim 1, wherein heat treating precipitated $\alpha$-$Fe_2O_3$-based particles of the said catalyst particles is carried out at a temperature of 380° C.

5. The process of claim 1, wherein heat treating precipitated $\alpha$-$Fe_2O_3$-based particles is conducted for at least 0.1 hours.

6. The process of claim 1, wherein heat treating precipitated $\alpha$-$Fe_2O_3$-based particles is conducted for from 0.5 hours to 4 hours.

7. The process of claim 1, wherein the self-supported precipitated $\alpha$-$Fe_2O_3$-based Fischer-Tropsch catalyst particles have an average observed Fischer-Tropsch activity in excess of 1.2 under low temperature Fischer-Tropsch operating conditions.

8. A process for synthesis of a Fischer-Tropsch product, the process comprising:

providing self-supported precipitated $\alpha$-$Fe_2O_3$-based Fischer-Tropsch catalyst particles, wherein the self-supported precipitated $\alpha$-$Fe_2O_3$-based Fischer-Tropsch catalyst particles are produced by heat treating precipitated $\alpha$-$Fe_2O_3$-based particles at a temperature of from 320° C. to 500° C., whereby breakage resistance of the catalyst particles is increased; and contacting a synthesis gas with the self-supported precipitated $\alpha$-$Fe_2O_3$-based Fischer-Tropsch catalyst particles in a Fischer-Tropsch slurry-bed reactor, whereby a Fischer-Tropsch product is obtained, wherein the increased breakage resistance of the catalyst particles inhibits formation of catalyst fines in the Fischer-Tropsch slurry-bed reactor, such that performance of a solid separation system employed in the process is maintained.

9. The process of claim 8, wherein heat treating precipitated $\alpha$-$Fe_2O_3$-based particles is carried out at a temperature of from 360° C. to 500° C.

10. The process of claim 8, wherein heat treating precipitated $\alpha$-$Fe_2O_3$-based particles is carried out at a temperature of from 360° C. to 390° C.

11. The process of claim 8, wherein heat treating precipitated $\alpha$-$Fe_2O_3$-based particles of the said catalyst particles is carried out at a temperature of 380° C.

12. The process of claim 8, wherein heat treating precipitated $\alpha$-$Fe_2O_3$-based particles is conducted for at least 0.1 hours.

13. The process of claim 8, wherein heat treating precipitated $\alpha$-$Fe_2O_3$-based particles is conducted for from 0.5 hours to 4 hours.

14. The process of claim 8, wherein the self-supported precipitated $\alpha$-$Fe_2O_3$-based Fischer-Tropsch catalyst particles have an average observed Fischer-Tropsch activity in excess of 1.2 under low temperature Fischer-Tropsch operating conditions.

15. The process of claim 8, wherein the self-supported precipitated $\alpha$-$Fe_2O_3$-based Fischer-Tropsch catalyst particles have an average observed Fischer-Tropsch activity in excess of 1.2 for at least 48 hours under low temperature Fischer-Tropsch operating conditions.

* * * * *